United States Patent [19]

Howell

[11] Patent Number: 4,863,693

[45] Date of Patent: Sep. 5, 1989

[54] ANALYSIS INSTRUMENT HAVING A BLOW MOLDED REACTION CHAMBER

[75] Inventor: Gary W. Howell, Elkton, Md.

[73] Assignee: E. I. Du Pont de Nemours and Company, Wilmington, Del.

[21] Appl. No.: 139,108

[22] Filed: Dec. 23, 1987

Related U.S. Application Data

[63] Continuation of Ser. No. 642,814, Aug. 21, 1984, abandoned.

[51] Int. Cl.[4] ............... G01N 35/04; G01N 37/00
[52] U.S. Cl. ......................... 422/64; 356/246; 356/440; 422/63; 422/65; 422/66; 436/44
[58] Field of Search ............... 53/202, 381, 474, 459, 53/453, 560; 422/64–67, 102, 104; 356/244, 286, 436, 440, 422; 436/44

[56] References Cited

U.S. PATENT DOCUMENTS

| | | | |
|---|---|---|---|
| D. 266,589 | 10/1982 | Gilford | D24/31 |
| 3,190,731 | 6/1965 | Weiskopf | 23/292 |
| 3,323,274 | 6/1967 | Justus | 53/30 |
| 3,346,464 | 10/1967 | Ernst | 435/31 |
| 3,437,447 | 4/1969 | Harmon | 422/64 |
| 3,477,821 | 11/1969 | Hamilton | 23/253 |
| 3,477,822 | 11/1969 | Hamilton | 422/61 |
| 3,480,398 | 11/1969 | Hamilton | 23/253 |
| 3,480,399 | 11/1969 | Hamilton | 23/253 |
| 3,497,320 | 2/1970 | Blackburn et al. | 436/44 |
| 3,504,376 | 3/1970 | Bednar et al. | 23/230 |
| 3,545,934 | 12/1970 | Dryden et al. | 422/61 |
| 3,545,935 | 12/1970 | Kearns | 23/253 |
| 3,554,705 | 1/1971 | Johnson et al. | 23/253 |
| 3,557,489 | 1/1971 | Ferrand | 47/37 |
| 3,582,283 | 6/1971 | Mirasol, Jr. | 23/253 |
| 3,582,285 | 6/1971 | Hamilton | 23/259 |
| 3,620,678 | 11/1971 | Guigan | 422/66 |
| 3,691,017 | 9/1972 | Brown et al. | 195/103 SR |
| 3,698,822 | 10/1972 | Polanyi | 356/246 |
| 3,756,884 | 9/1973 | Hagino | 156/145 |
| 3,776,375 | 12/1973 | Rohdin | 206/45.34 |
| 3,788,815 | 1/1974 | Rohrbaugh | 23/253 R |
| 3,788,816 | 1/1974 | Rohrbaugh et al. | 422/64 |
| 3,808,772 | 5/1974 | Turtschan | 53/559 X |
| 3,912,080 | 10/1975 | Winberg | 206/498 |
| 3,966,322 | 6/1976 | Greaves et al. | 356/39 |
| 3,994,594 | 11/1976 | Sandrock et al. | 356/246 |
| 4,053,284 | 10/1977 | Posch | 23/259 |
| 4,054,415 | 10/1977 | Seligson et al. | 422/64 |
| 4,083,638 | 4/1978 | Sandrock et al. | 356/246 |
| 4,090,791 | 5/1978 | Siddiqi et al. | 356/414 |
| 4,111,304 | 9/1978 | Lucas | 206/534 |
| 4,218,510 | 8/1980 | Willson | 428/349 |
| 4,234,538 | 11/1980 | Ginsberg et al. | 422/64 |
| 4,251,159 | 2/1981 | White | 356/246 |
| 4,263,256 | 4/1981 | Morle | 422/66 |
| 4,265,070 | 5/1981 | Mainberger et al. | 53/559 X |
| 4,303,616 | 12/1981 | Kano et al. | 422/102 |
| 4,325,910 | 4/1982 | Jordan | 422/64 |
| 4,329,061 | 5/1982 | Snook et al. | 356/414 |
| 4,349,510 | 9/1982 | Kolehmainen et al. | 422/66 |
| 4,466,740 | 8/1984 | Kano et al. | 356/246 |
| 4,528,159 | 9/1985 | Liston | 422/65 |

FOREIGN PATENT DOCUMENTS

| | | |
|---|---|---|
| 070623 | 1/1983 | European Pat. Off. |
| 2163590 | 7/1972 | Fed. Rep. of Germany |
| 3230901 | 3/1983 | Fed. Rep. of Germany |
| 1463127 | 11/1966 | France |
| 0402392 | 5/1966 | Switzerland |
| 8300296 | 2/1983 | World Int. Prop. O. |

Primary Examiner—Michael S. Marcus

[57] ABSTRACT

An analysis instrument is characterized by a rotatable mold ring onto which is drawn superimposed sheets of plastic material. The inner sheet is softened and formed into an indented mold cavity and the outer sheet sealed thereover to define a partially closed sample chamber, or cuvette. A sample to be analyzed is introduced into the chamber. Any of the chambers may have selectively introduced thereinto a suitable reagent and the reaction occurring in any chamber may be selectively monitored at any predetermined circumferential location of the mold ring.

31 Claims, 5 Drawing Sheets

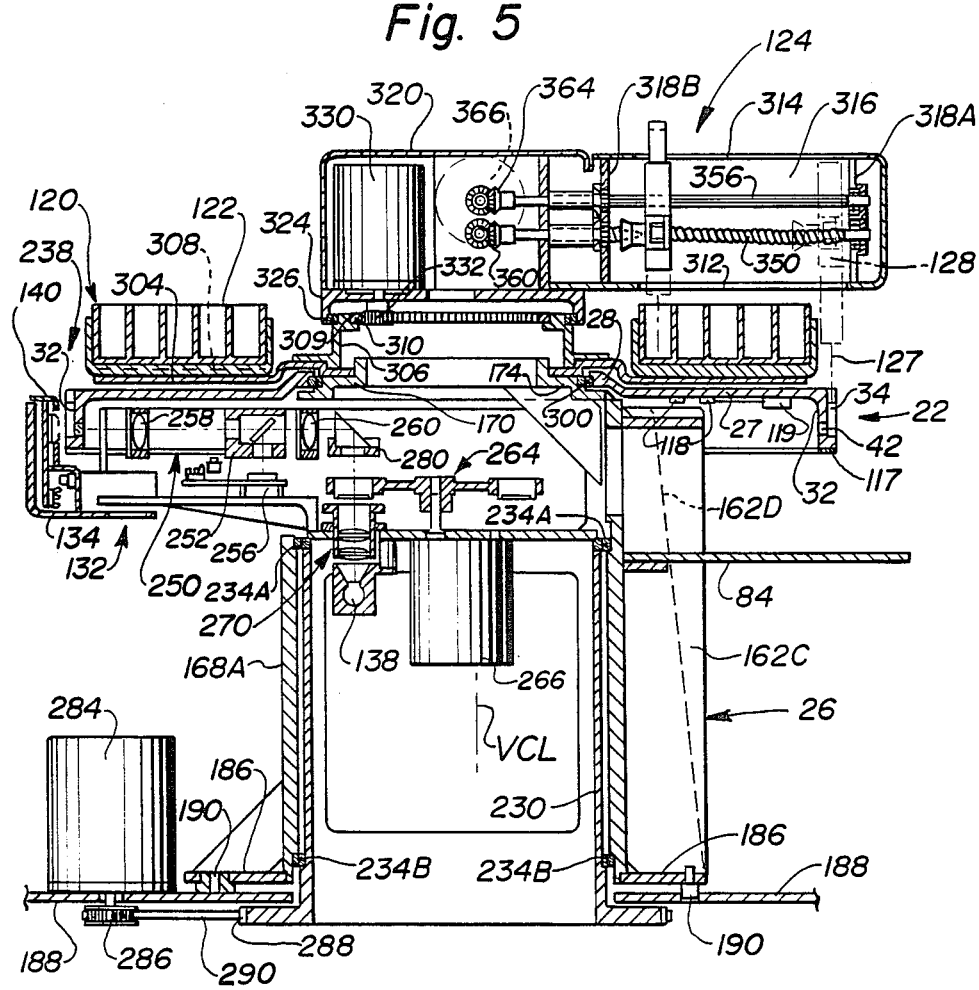
Fig. 5
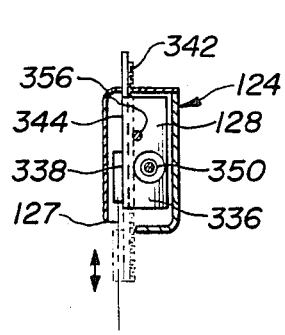
Fig. 11
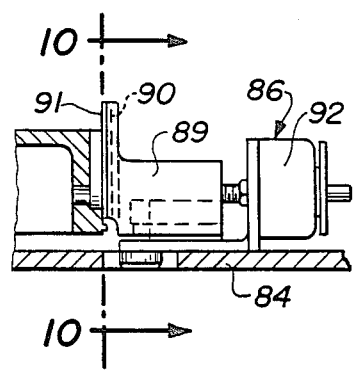
Fig. 9
Fig. 10

ANALYSIS INSTRUMENT HAVING A BLOW MOLDED REACTION CHAMBER

This application is a continuation of application Ser. No. 642,814, filed 8/21/84, abandoned.

Field of the Invention

This invention relates to a chemical analysis instrument and, in particular, to an analysis instrument in which the reaction chamber, or cuvette, is produced within the instrument.

Description of the Prior Art

Most of the known instruments used for the chemical analysis of a patient's body liquid utilize reaction chambers, or cuvettes, which have been formed prior to their introduction into the instrument. Some of such preformed chambers may also contain appropriate chemical reagents to which a sample of the material under test, e.g., a volume of a patient's body liquid, is added. However, chemical analysis of a sample using such preformed chambers have associated with it a relatively high economic cost due to the cost entailed with the prior formation of the chambers.

Accordingly, it is believed to be advantageous to provide an analysis instrument in which the reaction chamber or cuvette wherein occurs the reaction between a sample under test and the reagent is formed within the analysis instrument itself. Such an instrument is perceived to provide an economic advantage in that it eliminates the cost of prior formation of the chamber and thereby reduces the cost of each unit test.

In most present analysis instruments the introduction of the sample liquid under test into the reaction chamber, as well as the addition of the reagent into the sample, occurs at precisely defined points along the chamber's path of travel through the instrument. Moreover, the site at which the reaction is monitored is also precisely fixed along the travel path. As a result, most analysis instruments appear to be unable to provide a mechanism which can accommodate variations in the sample reaction time. Alternatively stated, because of the relative inflexibility as to the points of sample introduction, reagent introduction and reaction monitoring most present analysis instruments appear unable to provide an indication of the state of a reaction until a predetermined reaction time has elapsed.

Accordingly, it is also believed desirable to provide an analysis instrument which will permit flexibility with regard to the points or relative times at which sample and reagent are introduced into the sample chamber or cuvette as well as flexibility as to the time (or times) during the reaction at which monitoring of the reaction during the sample and the reagent may be made.

SUMMARY OF THE INVENTION

In accordance with the present invention an analysis instrument comprises a support column having a mold member, preferably in the form of a ring, rotationally mounted thereto. The mold ring has a plurality of indented mold cavities formed on the periphery thereof. A portion of each of the mold cavities is defined by a material transparent to an interrogating radiation. The instrument further includes means for placing a first, inner, and a second, outer, piece of plastic material into superimposed relationship around a predetermined portion of the periphery of the mold ring over a cavity therein as the ring is rotated with respect to the support column. An air jet arrangement directs a jet of heated air at the inner of the plastic pieces as it is drawn onto the ring to soften the same and cause it to deform into close contact with each mold cavity and into a thermally bonded relationship with the transparent portion of the mold cavity. A thermal sealing device is provided for securing the inner to the outer piece along an interface that surrounds the deformed portion of the inner sheet so as to define a partially enclosed reaction chamber, or cuvette. The inner and outer pieces of plastic material are spaced apart by a path length that lies within a predetermined close tolerance of a predetermined path length. As a result, in accordance with this invention, low cost, high precision, optical grade reaction chambers may be reproducibly formed in a given mold cavity.

A sample dispensing station is provided for introducing a sample of a material under test into the chamber. A reagent dispensing arrangement is mounted for movement with respect to the mold ring and is adapted to dispense reagent into the chamber at any selected relative position around the periphery of the mold ring. In addition, an analysis monitoring device, such as a photometer, is rotatably mounted with respect to the mold ring and positionable at any selected position about the periphery of the mold ring to thereby monitor the contents of the reaction chamber at that location on the mold ring.

A second sealing arrangement may be provided at any suitable location with respect to the mold ring to complete the sealed interface between the inner and outer pieces and permit the sanitary disposal of the reaction chambers.

BRIEF DESCRIPTION OF THE DRAWINGS

The invention may be more fully understood from the following detailed description thereof taken in connection with the accompanying drawings which form a part of this application and in which:

FIG. 5 is a side elevation view taken along section lines 5—5 of FIG. 4 showing an instrument in accordance with the present invention;

FIGS. 9 and 10 are, respectively, a side elevation and front elevation view of a heat sealing assembly used in an instrument in accordance with the present invention; and, FIG. 11 is an elevation view of a carrier for a reagent dispensing tube for an instrument in accordance with the present invention.

DETAILED DESCRIPTION OF THE INVENTION

Figure 1:
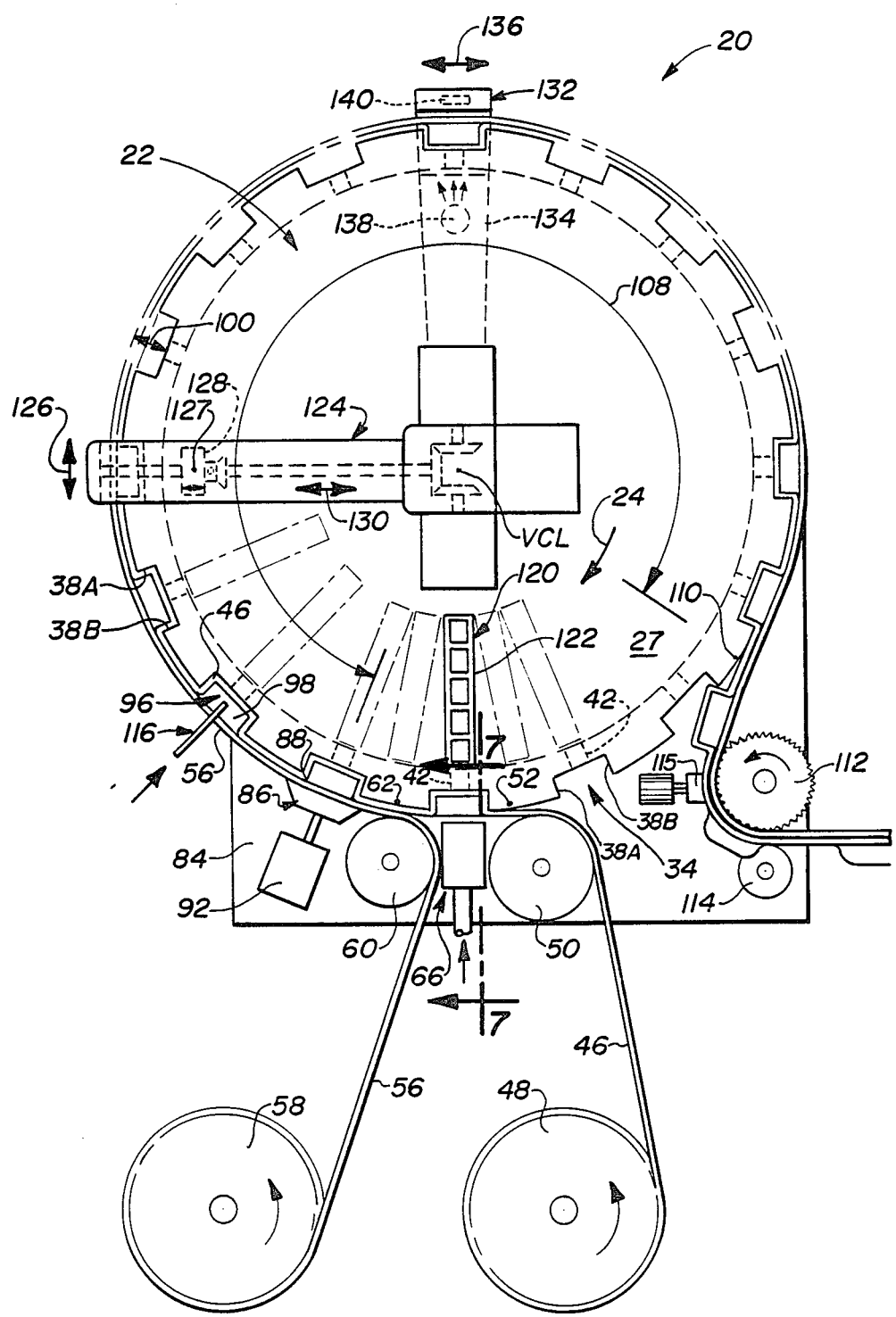
FIG. 1 is a highly stylized schematic representation, in plan, of an analysis instrument embodying the teachings of the present invention.

Throughout the following detailed description, similar reference numerals refer to similar elements and all figures of the drawings.

With reference to FIG. 1 shown in a highly stylized schematic representation of an analysis instrument generally indicated by reference character 20 in accordance with the present invention. The instrument 20 includes a mold ring generally indicated by reference character 22 mounted for rotational movement by means of an arrangement to be described about a vertical central axis VCL in a predetermined direction indicated by the arrow 24 with respect to a fixed support column, or base, 26 (best shown in FIGS. 5 and 6).

Figure 2:
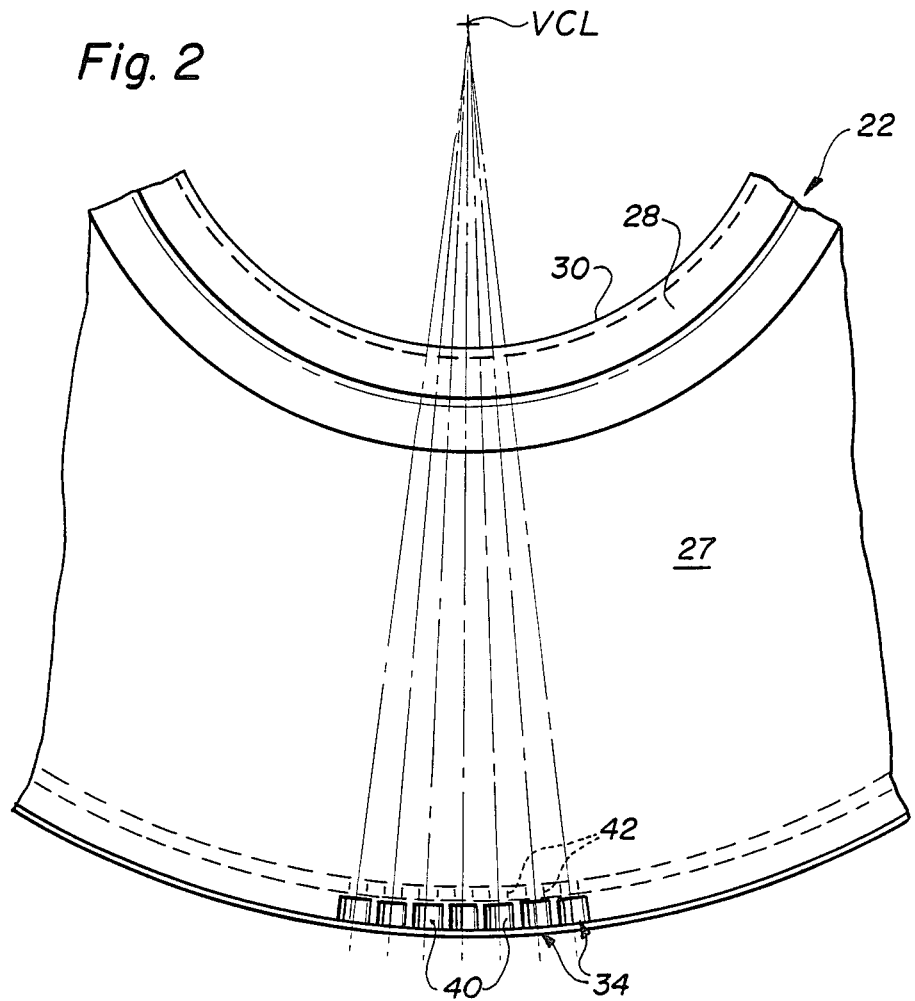
FIG. 2 is an enlarged plan view of a portion of the mold ring shown in FIG. 1.
Figure 3:
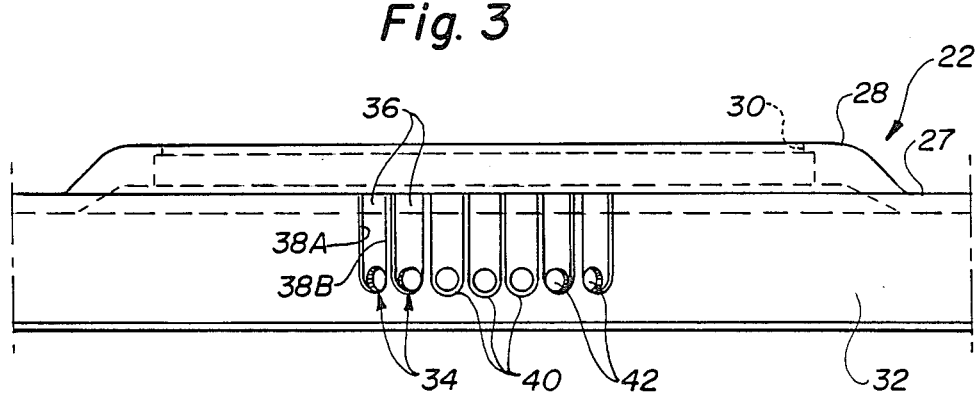
FIG. 3 is a side elevation view of the portion of the ring shown in FIG. 2.

As seen from FIGS. 1 through 3 the mold ring 22 is a generally circular member that has a planar annular portion 27 and a central upraised region 28 with an opening 30 therein. Of course, the mold member may take any predetermined configuration other than circular, if desired. The ring 22 turns downward at its periphery to define a depending skirt 32. On the periphery of the ring 22 an array of mold cavities 34 is defined by indentations in the skirt 32. Any predetermined number of mold cavities may be indented into the periphery of the mold member. In the preferred embodiment, one hundred fifty cavities are equiangularly arrayed about the periphery of the mold ring 22.

Each mold cavity 34 is formed by a circumferentially extending back wall 36 and confronting radial side walls 38A, 38B. The cavity 34 is closed at its lower end by a circular shelf surface 40. A portion of the back wall 36 of each mold cavity 34 includes a window 42 (perhaps best seen in FIG. 7) formed of a material transparent to interrogating radiation. Suitable for use as the window 42 as a clear quartz or plastic material.

Referring again to FIG. 1 a first, inner, web or piece 46 of plastic material is drawn from a suitable supply reel 48 and is guided over a guide spool 50 onto the periphery of the mold ring 22 as the same as rotated in the direction of rotation 24 past an inner web application point 52. A second, outer, web or piece 56 of plastic material is guided from a suitable supply reel 58 over a second guide spool 60 and placed onto the mold ring 22 in superimposed relationship with respect to the inner web 46 at an outer web application point 62.

An air jet arrangement 66 (also shown in FIGS. 7 and 8) is disposed in a predetermined operative position along the mold ring 22 intermediate the web application points 52 and 62. The air jet arrangement 66 is operative to direct a jet of heated air toward the inner web 46 to soften the same. The jet of heated air directed toward the softened portion of the inner web 46 then causes it to deform into a close fitting contact with the mold cavity 34 and to adhere closely to the boundary walls 36, 38A, 38B and 40 of the cavity 34. The inner web 46 is also urged into a thermally bonded contact with the window 42 provided in each cavity 34. Thereafter, a jet of ambient temperature air cools the deformed portion of the inner web 46 while holding it in place.

The definition of the thermal bond between the deformed portion of the inner web and the window 42 serves to precisely locate the inner wall of a reaction chamber to be formed such that precise chambers may be reproducibly formed in a given mold cavity.

Figure 7:
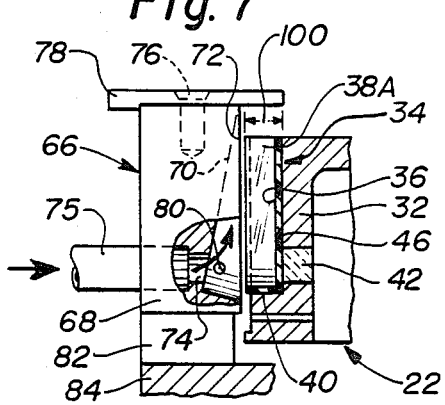
FIGS. 7 and 8 are, respectively, a side elevation and a plan view of an air jet assembly used in an instrument in accordance with the present invention.
Figure 8:
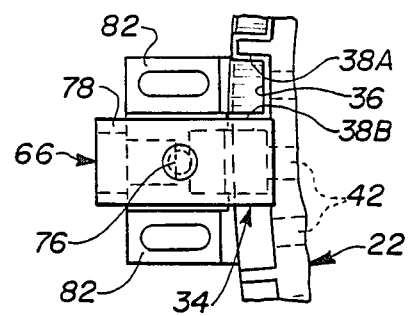

With reference to FIGS. 7 and 8 the air jet arrangement 66 includes a shoe 68 having a contoured hollow 70 formed on the face 72 disposed in confronting relationship to the mold ring 22. The air or gas outlet 74 is provided at the lower end of the hollow 70 and is connected via a conduit 75 to a suitable source of heated and ambient air. Attached to the upper end of the shoe 68 by any suitable means, such as a bolt 76, is a shroud 78. The shroud 78 projects radially inwardly to overhang the mold cavity 34. Heated or ambient air emanates from the outlet 74 and is directed toward the mold cavity 34. The contour of the hollow 70 tapers to maintain fluid pressure as the fluid moves upwardly from the outlet 74. The temperature of the fluid is monitored by a thermocouple 80 provided in the shoe 68. The shoe 68 is mounted by support feet 82 to a mounting plate 84 itself connected to the support column 26 (see also FIG. 5).

Downstream of the outer web application point 52 a thermal sealing arrangement 86 is mounted to the plate 84 and is provided for sealing the outer web 56 to the inner web 46 along a sealed interface 88. The sealing arrangement 86, which is shown in FIGS. 9 and 10, takes the form of a resistance heater element although other sealing devices, such as an ultrasonic welding device may be used.

As best seen from FIGS. 9 and 10 the sealing arrangement 86 includes a block 89 carrying a J-shaped heating element 90. The heating element is covered by a sheath 91 of a nonsticking material, such as that sold by Dodge Industries, Hoosick Falls, N.Y., under the trademark FLUORAGLAS. The sealing block 89 is moved into and out of contact with the superimposed webs 46 and 56 by an actuator 92.

As a result of the action of the air jet arrangement 66 and the sealing arrangement 86 a sample chamber or cuvette 96 is formed in each mold cavity 34. The reaction chamber 96 defines a partially enclosed sample reaction volume 98 between the deformed inner web 46 and the outer web 56. By "partially enclosed" it is meant that the chamber 96 so formed presents some aperture by which access may be had to the volume 98 defined within the bonded inner and outer webs. The chamber 96 is thus not necessarily a fully closed region but is open at the top to permit access to the volume 98 on the interior thereof to facilitate introduction of sample and reagent, as will be discussed.

Suitable for use as the webs 46 and 56 are any optical grade thermoplastic materials. By "optical grade" it is meant that the web is transparent to interrogating radiation without distortion or significant attenuation, as by defects, fisheyes and aberrations. For example the inner web 46 and outer web 56 are preferably fabricated of heat softenable plastic material such as a material formed from an ionomer resin manufactured and sold by E. I. du Pont de Nemours and Company, Inc. under the trademark SURLYN. The outer web 56 is held in relatively greater tension than the web 46 such that the outer boundary of each chamber 96 is drawn tightly to lie substantially chordal of the mold ring 22. That is, in the plane of FIG. 1, the radially outer boundary of the reaction chamber 96 is defined by the inner surface of the outer web 56 is a substantially straight line defined between the radial side walls 38A, 38B provided on the periphery of the mold ring 22. As a result of the thermal bonding of the inner web 46 to the window 42 and the chordal relationship of the outer web 56 to the mold ring 22 the reaction chamber 96 so defined exhibits a precise path distance, or path length, 100. The path length 100 lies within a predetermined close tolerance (typically one percent) of a predetermined path distance (typically 0.198 inch). In accordance with this invention such precisely formed reaction chambers may be repeatedly and reproducibly formed in any given mold cavity 34.

Of course, any other suitable materials may be used for the inner and outer webs and remain within the contemplation of the present invention. For example, the inner and outer webs may be sliced from a common stock and folded. Alternatively, the webs 46 and 56 may be fabricated from a laminate of nylon (as the exterior ply) and the above-cited ionomeric material as the interior ply.

The strip of adjacent chambers formed in the manner outlined above is trained about the periphery of the mold ring 22 for a predetermined angular distance 108 defined between the application point 52 and a take-off point 110. The strip is removed from the mold ring 22 in the vicinity of the take-off point 110 by the action of a take-off capstan wheel 112. A follower 114 is biased into contact with the capstan 112. The capstan 112 is driven by a drive motor (not shown) which is mounted in a driving relationship to the wheel 112 beneath the mounting plate 84. In the preferred embodiment of the invention it is the action of the capstan wheel 112 that supplies the motive energy for rotation of the mold ring 22 about the vertical center line VCL ring 22 in the direction 24. This action serves to precisely displace each reaction chamber to any predetermined angular location (within the angular range 108) with respect to the axis of rotation VCL. Of course any suitable drive arrangement for rotating the mold ring 22 may be used provided adequate tension is maintained in the webs 46, 56.

If desired, at any predetermined point along the circumference of the ring 22 or the path of the strip toward the wheel 112 a closure device 115 may be mounted to the plate 84 to seal the open top of the chamber 96 to facilitate sanitary disposal. In FIG. 1, the closure device 115 is provided intermediate the spool 114 and the take-up wheel 112.

Located at any predetermined angular location downstream of the sealing assembly 86 is a sample inject mechanism 116 adapted to introduce a sample of material under test, typically the body liquid of a patient, into the open top of the chamber 96 formed as described above. Any suitable sample inject mechanism may be used.

To maintain the proper reaction temperature the ring 22 may be heated and maintained at a suitable temperature by heating arrangement. The heating arrangement in the preferred case takes the form of an annular resistance heater ring 117 (FIG. 5) disposed on the undersurface of the depending skirt 32. The ring 117 is supplied current by an array of slip rings 118 carried on the undersurface of the mold ring 22 (FIG. 5). A suitable controller 119 is also provided. Heating the reaction mixture by conduction in this manner is believed advantageous because it minimizes air movement around the top of the reaction chamber 96 and thus minimizes evaporation.

The upper surface of the planar annular portion 27 of the mold ring 22 carries a reagent supply arrangement 120 having an array of reagent containers 122 disposed in substantially radial directions from the vertical center of rotation VCL of the ring 22. The reagent containers 122 may be refrigerated or cooled, if desired, as is discussed herein.

Figure 4:
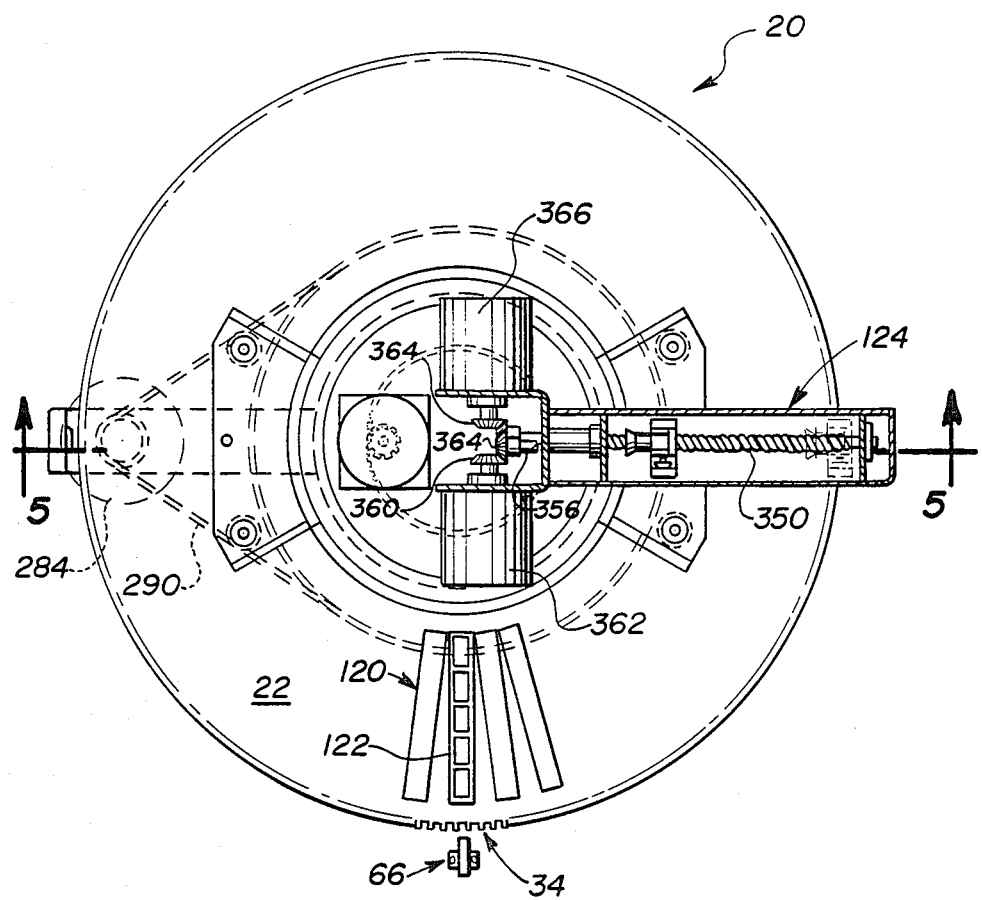
FIG. 4 is a plan view of an analysis instrument in accordance with the present invention.

A reagent supply arm 124 is mounted with respect to the mold ring for relative rotational movement with respect thereto in the direction of the double arrow 126 to provide the capability to randomly dispose the arm 124 at any selected angular location about the axis VCL. As best seen in FIGS. 4, 5 and 11 the reagent supply arm 124 includes a reagent dispensing tube, typically a supply needle, 126 carried by a carrier 128. The dispensing tube 126 is movable in substantially radially inward or radially outward directions 130 with respect to the mold ring 22 to efficiently and effectively aspirate a selected reagent from any one of the segmented portions of the containers 122 and to deposit the same into one of the fully formed chambers 96 disposed at any angular position within the predetermined range 108 of angular distances arranged around the periphery of the mold ring 22. Due to the flexibility of the reagent introduction provided by the structure above described the instrument 20 in accordance with the present invention contemplates the possibility, among others discussed herein, of sample initiated reactions. That is, the appropriate reagent may be introduced into a selected chamber 96 prior to the introduction of a sample into that chamber (i.e., at a point "upstream" of the sample inject mechanism 118 intermediate that mechanism and the sealing assembly 86). Thus, the introduction of the sample would serve to initiate the reaction with the reagent.

A reaction monitoring device 132, such as a photometer, is mounted in a support arm 134 disposed beneath the mold ring 22 and mounted for independent rotational movement in the direction of the double arrows 136 with respect thereto. The arm 134 brackets the skirt portion 32 of the mold ring 22 at both the radially inward and radially outward sides thereof. The monitoring device 132 includes a source of interrogating radiation indicated diagrammatically in FIG. 1 at 138 which is mounted in the arm 134 at a point radially inward of the skirt 32 formed in the mold ring 22. A radiation detector diagrammatically in FIG. 1 indicated at 140, is mounted in the support arm 134 radially outward of the skirt 32. Of course, these relative locations of the source 138 and detector 140 may be reversed. Moreover, the invention also contemplates the use of a grating photometer as the monitoring device. Such a photometer includes a source of interrogating radiation which is directed through the chamber 96 and the window 42 to a diffusion grating which separates the radiation incident thereon into its component wavelengths. These components are directed to the detector. Any convenient relative radial positioning of these elements may be used.

Because of the described constructional relationship the instrument 20 in accordance with the present invention is capable of monitoring the reaction occuring in any chamber 96 disposed at any predetermined point on the mold ring 22 along the predetermined angular distance 108. As a consequence a reaction may be observed throughout its cycle and not merely at a time when the reaction chamber reaches a fixed observation point. As will be seen the particular construction of the support column 26 and the mounting of the monitoring device to the instrument serves to limit the range of angular positions at which the monitoring device 13 positionable. However, other alternate constructions and/or mounting arrangements may be used whereby the monitoring device is positionable at any predetermined position along the circumference of the ring 22 and such mounting is to be construed as lying within the contemplation of the present invention. Furthermore, it should be noted that the positions of either the reagent supply 120 and/or the monitoring device 132 may be altered to other convenient positions and remain within the contemplation of the invention.

Figure 6:
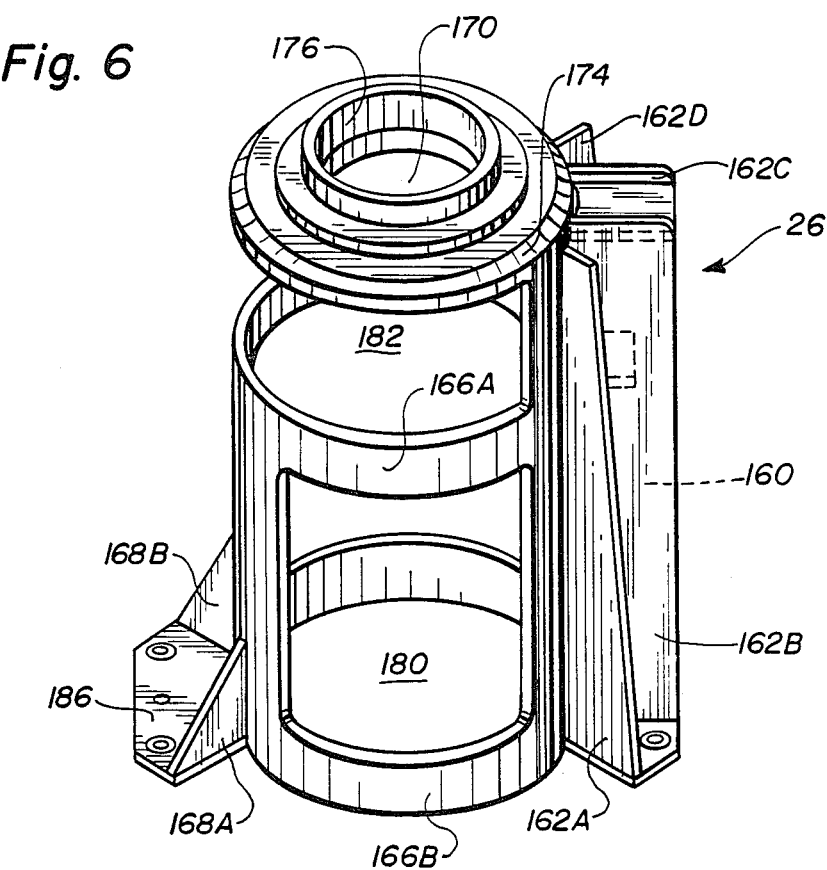
FIG. 6 is a perspective view of the support column of an instrument in accordance with the present invention.

A more detailed constructional description of the invention may be understood with reference to FIGS. 4, 5 and 6. The instrument 20 includes a support base or column 26 (FIG. 4, 6) in the form of a generally cylindrical cast member. The column 26 has a spine portion 16D formed with four vertically adjacent splines 162A through 162D. From the spine 160 upper and lower cylindrical bands 166A and 166B respectively extend horizontally. Vertically extending supports 168A and 168B interconnect the bands 166 and impart structural rigidity to the same. The spine 160 extends vertically above the upper band 166A and supports in cantilevered relationship a cap 170. The cap 170 has a stepped portion 174 about its periphery. The cap 170 has an access opening 176 formed therein that communicates with the hollow cylindrical central region 180 of the support column 26. The peripheral edges of the stepped portion 174 of the cap 170 and the upper band 166A cooperate to define a substantially circumferentially extending space 182 that extends angularly for a distance encompassing the angular distance 108 between the two angularly outward edges of the spine 160. The support plate 84 projects outwardly in a substantially horizontal orientation from the spine 160. As noted, the plate 84 forms the base support for the air jet arrangemenet 66 (FIGS. 7 and 8) the rollers 50 and 60, and the sealing arrangement 92, 86 (FIGS. 10 and 11), the capstan 112 and the wheel 114, and the second sealing arrangement 115. A planar mounting flange 186 is connected to the lower surface of the spine 160 and of the struts 168 and is secured by any suitable means of attachment to the structural framework 188 of the instrument as shown at 190.

The reaction monitoring device 132 is disposed within the central region 180 of the support column 26. This device includes a substantially cylindrical barrel portion 230 which is mounted for rotational movement on upper and lower bearings 234A and 234B, respectively. Extending radially outwardly from the barrel portion 230 is the support arm 134. The support arm 134 is grooved, as at 238, near the outward end thereof. The detector 140 and associated amplification electronics is housed in the radially outer end of the arm 134. An optics module 250 is removably supported in the major portion of the arm 134 located radially inwardly of the groove 238. The optics module 250 includes a beam splitter 252 and a reference transducer 256 and associated amplification electronics. Focusing lenses 258 and 260 are housed in the arm 134 to concentrate radiation passing through the beam splitter 252 and direct the same through the window 42 and the chamber 96 to the detector 140.

Mounted within the barrel portion 230 of the photometer 132 is a filter wheel assembly 264 driven by a suitable drive motor 266. The source 138 of interrogating radiation is also mounted within the barrel 230 proximal to the filter wheel 264. Interrogating radiation from the source 138 passes through a focusing lens arrangement 270, through a selected filter in the wheel 264 and is directed by a mirror 280 toward the optics module 250. Appropriate control electronics are also disposed in the barrel 230.

Motive energy for the rotation of the photometer assembly 96 with respect to the support column 230 is provided by a drive motor 284 mounted to any convenient location within the housing of the instrument. A drive gear 286 connected to the shaft of the motor 284. The motor 284 is interconnected to a circle gear 288 affixed to the exterior of the photometer barrel 230 by a belt 290. Accordingly, rotation of the motor 284 in an appropriate angular direction rotates the photometer with respect to the support column 26 and thereby positions the photometer arm 134 at any angular location along the portion 108 of the circumference of the mold ring 22.

The mold ring 22 is mounted for rotational movement on a bearing arrangement 300 disposed between the upraised central region 28 of the ring 22 and the step 174 of the cap portion 170 of the column 26.

The reagent supply arrangement 120 includes an annular planer tray 304 having a central post 306. The individual reagent containers 122 are supported on the tray 304. The tray 304 is fabricated of a heat conductive material, such as aluminum, and is provided with a labyrinth array of coolant passages 308. Coolant liquid may be pumped through the passages 306 to maintain reagents in the container 122 at a predetermined desired temperature. The tray 122 is supported away from the surface of the ring 22 and a layer of a suitable thermal insulation (not shown) may be disposed between the tray 122 and the ring 22.

The foot of the post 306 is secured to the cap 170 of the support column 26 by any suitable mounting arrangement which nonrotatably secures the tray 306 with respect to the column 26. The post 308 at its upper end is provided with a central opening 309 on which is disposed a circular gear 310.

The reagent supply arm 124 includes a base plate 312 and a cover plate 314. The plates 312 and 314 are spaced apart to define an enclosed region 316. The arm 124 has upstanding end plates 318A and 318B mounted therein. The inner end of the arm 124 is connected to a hub 320 having a downwardly projecting flange 324. The supply arm 124 is rotationally mounted with respect to the base 26 by means of a bearing assembly 326 provided between the radially inner surface of the flange 324 and the radially outer surface of the post 308.

Motive force for the rotation of the supply arm 124 with respect to the support column 26 is provided by a stepper motor 330 mounted in the hub 320. The shaft of the motor 330 projects downwardly from the hub 320 and is provided with a pinion 332 which engages the circular gear 310 mounted to the post 308.

As seen in FIG. 11 the reagent dispensing tube 128 further includes a carrier block 336 having a shoe 338 which supports the dispensing tube 126. A gear rack 342 attached to the shoe 338 rides in tracks 344 provided in the block 336. The reagent needle block 336 is movable radially with respect to the arm 124 on a spiral gear shaft 350 and a splined shaft 356 which are each respectively rotationally mounted between the end plates 318A and 318B. The spiral shaft 350 is mounted to the block 336 while the splined shaft 356 is engagable with the gear rack 342 affixed to the block. The shaft 350 is connected at its radially inner end via a bevel gear 360 to a first drive motor 362 (FIG. 4). The action of the motor 362 serves to displace the needle block assembly 336 radially outward or radially inward. The splined shaft 356 is connected via a bevel gear 364 to a second drive motor 366. Vertical movement of the needle 126

(once the needle block 336 is radially positioned in a predetermined location) is afforded by the vertical drive motor 336 connected to the splined shaft 356.

In operation, superimposed plastic leader strips from the inner and outer web supply reels are trained over the respective spools 50 and 60, around the periphery of of the mold 22, about the capstan wheel 112 and the back-up wheel 114. Rotation of the capstan wheel 112 provides the motive energy for rotation of the ring 22 and the advancement of the chamber 96 formed in the manner discussed in the direction of travel 24. A jet of heated air from the air jet arrangement 66 softens the inner web 46 and forces the softened material of the inner web 46 into intimate contact with the boundaries of the mold cavity 34 then in proximity to the air jet arrangement. The inner web 46 takes the form of the mold cavity 34 with the web being disposed in thermally bonded relationship with the window portion 42 of the cavity 34. The tapered surface 70 of the shoe 68 maintains sufficient pressure on the web 46 to force the same completely into the cavity 34.

Rotation of the mold ring 22 in the direction 24 displaces the mold cavities 34 lined with the inner web 46 past the outer web application point 62 whereat the outer web 56 is placed thereover in radially superimposed relationship. Continued rotation of the ring 22 places the superimposed webs 46 and 56 in the vicinity of the sealing arrangement 86. This arrangement 86 is advanced radially inward by action of the actuator 92 to contact the webs and thermally bond the same together. Due to the shape of the heating element 90 the webs are bonded along a substantially J-shape. The webs are further joined as the next-successive cavity 34 is brought into position with respect to the heating element. Thus, the vertical edge of the interface left open by the first-discussed heating is closed by the elongated leg of the J-shaped heater during the next successive heating. This action prevents repeated heat sealing along the same portion of the interface. In any event, as a result of the action of the sealing arrangement 86 the inner and outer webs are sealed along an interface 88 that serves to define a partially enclosed chamber 96 in the cavity 34. In accordance with the preferred embodiment of this invention the chambers 96 are accessible from directly vertically thereabove.

As the mold ring 22 is advanced the chambers 96 are provided with sample from the sample inject mechanism 118 and reagent via the reagent dispensing arrangement 120. It is noted that due to the ability of the reagent dispensing arrangement 120 to rotate over the entire circumference of the ring 22 reagent may be introduced into a chamber 96 prior to the point at which a sample is injected thereinto. Thus, a sample-initiated reaction may be provided by the instrument 20 in accordance with the present invention. Since the mold ring 22 is heated by the action of heating element 117 the correct temperature for the desired chemical reaction is maintained.

The reactions occurring in each chamber 96 may be monitored at any position within the predetermined angular range 108 by the monitoring device 132. Since the monitoring device is rotatably movable under the circumference of the ring 22 (save for that angular distance occupied by the spine 160 of the support column) the monitoring device 132 can be used to observe the reaction in a chamber 96 throughout the entire reaction cycle, not merely at a fixed point. Further, when coupled with the flexibility of reagent introduction imparted by the dispensing means above described, it is possible to monitor a chamber in blank (i.e., with no sample or reagent), a chamber with sample only (i.e., prior to sample introduction), a chamber with reagent only (a "reagent blank"), or a chamber with sample and reagent.

When the strip of chamber is stripped from the mold ring 22 the closure device 115 serves to fully enclose each chamber 96 to prevent runoff of reaction mixture and permit sanitary disposal thereof.

In view of the foregoing those skilled in the art may readily appreciate that an analysis instrument in accordance with the present invention is adapted to provide precise production on-board the mold member of optical grade reaction chambers, or cuvettes, at a low cost. Further, the instrument provides the capability for accurately transporting and maintaining the temperature of the reaction chambers so formed, for selectively positioning a reaction monitoring device and/or a reagent introducing device at any predetermined position with respect to the mold member, and for disposing of the chambers in a sanitary manner.

Those skilled in the art, having benefit of the teachings hereinabove set forth, may effect numerous modifications thereto. These modifications are to be construed as lying within the scope of the present invention, as set forth in the appended.

What is claimed is:

1. An analysis instrument adapted to form reaction chambers from plastic material within the instrument and to analyze a sample placed within the chambers so formed comprising:

a mold member having a plurality of mold cavities formed on a periphery thereof, a portion of each mold cavity being transparent to interrogating radiation;

means for placing an inner piece of plastic material on the mold member at a first application point;

means disposed in proximity to the mold member adjacent to the first application point for deforming the inner piece of plastic material into close contact with boundaries of the cavity then proximal to the deforming means and into bonded relationship with the transparent portion of the cavity;

means for placing an outer piece of plastic material on the mold member at a second application point spaced on the mold member from the deforming means, the second piece of plastic material being disposed in a superimposed relationship with respect to the first piece of plastic material such that the inner and outer pieces of plastic material are spaced apart by a distance lying within a predetermined close tolerance of a predetermined distance;

a sealing arrangement for joining the inner and outer pieces of plastic material together to define a partially enclosed reaction chamber therebetween; and a reaction monitoring device mounted for relative movement with respect to the mold member, the monitoring device being positionable adjacent to any one of a predetermined number of locations on the mold member having a reaction chamber therein, the monitoring device being operable to direct a beam of interrogating radiation through the transparent portion of the cavity of the mold member.

2. The analysis instrument of claim 1 further comprising:

a dispensing arrangement mounted for relative movement with respect to the mold member, the dispensing arrangement being positionable at any location about the periphery of the mold member.

3. The analysis apparatus of claim 1 wherein the mold cavity has a first and second wall and further comprising:
means for tensioning the outer piece of plastic material so that the same lies on a substantially straight line between the side walls of the mold cavity.

4. The analysis instrument of claim 1 further comprising:
means mounted to the mold member for maintaining the temperature thereof at a predetermined temperature level.

5. The analysis instrument of claim 4 further comprising:
a dispensing arrangement mounted for relative movement with respect to the mold member, the dispensing arrangement being positionable at any location about the periphery of the mold member.

6. The analysis instrument of claim 1 further comprising:
means for rotating the member about an axis of rotation, the rotating means comprising a driven member engaging the inner and outer pieces of plastic material such that movement of the driven member rotates the mold member.

7. The analysis instrument of claim 6 further comprising:
a dispensing arrangement mounted for relative movement with respect to the mold member, the dispensing arrangement being positionable at any angular location about the axis.

8. The analysis instrument of claim 6 further comprising:
means mounted to the mold member for maintaining the temperature thereof at a predetermined temperature level.

9. The analysis instrument of claim 8 further comprising:
a dispensing arrangement mounted for relative movement with respect to the mold member, the dispensing arrangement being positionable at any angular location about the axis.

10. An analysis instrument adapted to form reaction chambers from plastic material within the instrument and to analyze a sample placed within the chambers so formed comprising:
a mold ring having a plurality of mold cavities formed on a periphery thereof, a portion of each mold cavity being transparent to interrogating radiation;
means for placing an inner piece of plastic material on the mold member at a first application point;
an air jet arrangement disposed in proximity to the mold member adjacent to the first application point for directing a jet of heated air at the inner piece of plastic material to soften the same and cause it to deform into close contact with boundaries of the mold cavity then proximal to the deforming means and into a thermally bonded relationship with the transparent portion of the cavity;
means for placing an outer piece of plastic material on the mold ring at a second application point spaced on the mold ring from the air jet arrangement, the second piece of plastic material being disposed in a superimposed relationship with respect to the first piece of plastic material such that the inner and outer pieces of plastic material are spaced apart by a path length distance lying within a predetermined close tolerance of a predetermined distance;
a sealing arrangement for joining the inner and outer pieces of plastic material together along an interface that surrounds the deformed portion of the inner piece to define a partially enclosed reaction chamber between the inner and outer pieces of plastic material; and
a reaction monitoring device mounted for relative movement with respect to the mold member, the monitoring device being positionable adjacent to any one of a predetermined number of locations on the mold member having a reaction chamber therein, the monitoring device being operable to direct a beam of interrogating radiation through the transparent portion of the cavity of the mold member.

11. The analysis instrument to claim 10 further comprising:
means mounted to the mold ring for maintaining the temperature thereof at a predetermined temperature level.

12. The analysis instrument of claim 10 wherein the monitoring device includes a source of interrogating radiation disposed on one radial side of the reaction chamber and a radiation responsive element on the radially opposite side of the chamber.

13. The analysis instrument of claim 10 wherein the sealing arrangement comprises an air jet itself comprising a shoe with a hollow having a pressure equalizing profile and an outlet aperture at the base of the hollow.

14. The analysis instrument of claim 10 further comprising:
means for fully enclosing the reaction chamber prefatory to discarding the same.

15. The analysis instrument of claim 10 wherein the mold cavity has a first and second wall and further comprising:
means for tensioning the outer piece of plastic material so that the same lies on a substantially straight line between the side walls of the mold cavity.

16. The analysis instrument of claim 10 further comprising:
means for introducing a sample of material under test into the reaction chamber.

17. The analysis instrument of claim 16 further comprising:
a reagent dispensing arrangement mounted for relative movement with respect to the mold ring, the dispensing arrangement being positionable at any selected angular position about the mold ring.

18. The analysis instrument of claim 16 further comprising:
means mounted to the mold ring for maintaining the temperature thereof at a predetermined temperature level.

19. The analysis instrument of claim 16 further comprising:
means for rotating the member about an axis of rotation, the rotating means comprising a driven member engaging the inner and outer pieces of plastic material such that movement of the driven member rotates the mold member.

20. The analysis instrument of claim 19 further comprising:

means mounted to the mold ring for maintaining the temperature thereof at a predetermined temperature level.

21. The analysis instrument of claim 19 further comprising:
a reagent dispensing arrangement mounted for relative movement with respect to the mold ring, the dispensing arrangement being positionable at any selected angular position about the mold ring.

22. The analysis instrument of claim 10 further comprising:
means for rotating the member about an axis of rotation, the rotating means comprising a driven member engaging the inner and outer pieces of plastic material such that movement of the driven member rotates the mold member.

23. The analysis instrument of claim 22 further comprising:
a reagent dispensing arrangement mounted for relative movement with respect to the mold ring, the dispensing arrangement being positionable at any selected angular position about the mold ring.

24. The analysis instrument of claim 22 wherein the driven member comprises a capstan connected to the pieces of plastic material to draw the same onto the ring and simultaneously to rotate the ring.

25. The analysis instrument of claim 22 further comprising:
means mounted to the mold ring for maintaining the temperature thereof at a predetermined temperature level.

26. The analysis instrument of claim 10 further comprising:
a reagent dispensing arrangement mounted for relative movement with respect to the mold ring, the dispensing arrangement being positionable at any selected angular position about the mold ring.

27. The analysis instrument of claim 26 further comprising:
means for rotating the mold ring about an axis of rotation to displace the reaction chamber to any location with respect to the axis.

28. The analysis instrument of claim 26 wherein the reaction monitoring device is disposed below the mold ring while the reagent dispensing arrangement is disposed above the mold ring.

29. The analysis instrument of claim 26 wherein the dispensing arrangement is mounted above the mold ring and further comprising:
a reagent supply vessel disposed on an upper surface of the ring.

30. The analysis instrument of claim 29 wherein the dispensing arrangement includes a dispensing tube that is movably radially inwardly and outwardly of the ring to respectively communicate with the supply vessel and the reaction chamber.

31. The analysis instrument of claim 30 wherein the reagent supply vessel contains passages for the circulation of a cooling fluid therethrough.

* * * * *